(12) United States Patent
Kim et al.

(10) Patent No.: US 7,459,471 B2
(45) Date of Patent: Dec. 2, 2008

(54) INCLUSION COMPOUND COMPRISING CUCURBITURIL DERIVATIVES AS HOST MOLECULE AND PHARMACEUTICAL COMPOSITION COMPRISING THE SAME

(75) Inventors: Kimoon Kim, Pohang-shi (KR); Young Jin Jeon, Pohang-shi (KR); Soo Young Kim, Pohang-shi (KR); Young Ho Ko, Pohang-shi (KR)

(73) Assignee: Postech Foundation, Pohang-Shi (KR)

( * ) Notice: Subject to any disclaimer, the term of this patent is extended or adjusted under 35 U.S.C. 154(b) by 781 days.

(21) Appl. No.: 10/489,968

(22) PCT Filed: Sep. 18, 2002

(86) PCT No.: PCT/KR02/01755
§ 371 (c)(1),
(2), (4) Date: Mar. 18, 2004

(87) PCT Pub. No.: WO03/024978
PCT Pub. Date: Mar. 27, 2003

(65) Prior Publication Data
US 2004/0265237 A1      Dec. 30, 2004

(30) Foreign Application Priority Data
Sep. 18, 2001   (KR) ................ 2001-57573

(51) Int. Cl.
C07D 403/02  (2006.01)
A01N 43/64   (2006.01)
A61K 31/41   (2006.01)

(52) U.S. Cl. ............... 514/359; 548/300.1; 548/301.7; 548/302.7; 548/303.4

(58) Field of Classification Search ............ 548/300.1, 548/300.7, 302.7, 303.4
See application file for complete search history.

(56) References Cited

U.S. PATENT DOCUMENTS
5,965,118 A    10/1999   Duncan et al.

OTHER PUBLICATIONS

Mario Biogioni et al., "Electronic attack of [I(py)2]+(NO3-) on three-coordinate Pt0 precursors: Synthesis and In Vitro antitumor activity of water-soluble, five coordinate Pt2 complexes", European J. Of Inorganic Chemistry, 2000 (8), pp. 1717-1721, Wiley-VCH Verlag Gmbh, 2000.

M.B. de Oliveira et al., "New perfluorophthalate complexes of platinum(II) with chemotherapeutic potential", Metal-Based Drugs, 1996 3(3), pp. 117-122, Freund, 1996.

Ui-Rak Kim et al., "The study about interation of cis-diaminedichloroplatin (cis-DDP) complexes with DNA base, 1-methylcytosine, for development of anti-tumor drug", Taehan Hwahakhoe Chi, 1990 34(4), pp. 331-339, 1999.

Beverly A. Teicher et al., "Combination of etanidazole with cyclophosphamide and platinum complexes", Cancer dhemotherapy and Pharmacology, 1991 28(3), pp. 153-158, 1991.

Primary Examiner—James O. Wilson
Assistant Examiner—Paul V. Ward
(74) Attorney, Agent, or Firm—Rothwell, Figg, Ernst & Manbeck (57) ABSTRACT

The present invention provides an inclusion compound having a cucurbituril derivative of the formula 1 as a host molecule and a metal complex of the formula 2 as a guest molecule. A pharmaceutical composition having an anticancer effect can be obtained by using the inclusion compound according to the present invention. The pharmaceutical composition can prevent effective components from being biologically degraded in vivo and can exhibit continuous drug effect for a long time just by a single dosage by controlling the release time of the platinum complex once it reaches target tumor cells.

10 Claims, 2 Drawing Sheets

INCLUSION COMPOUND COMPRISING CUCURBITURIL DERIVATIVES AS HOST MOLECULE AND PHARMACEUTICAL COMPOSITION COMPRISING THE SAME

DETAILED DESCRIPTION OF THE INVENTION

Object of the Invention

Technical Field of the Invention and Related Art Prior to the Invention

The present invention relates to an inclusion compound and pharmaceutical composition containing the same.

Numerous anticancer agents using platinum complexes have been synthesized since the discovery of the anticancer effect of platinum complexes. However, the anticancer agents hitherto synthesized have not been satisfactory in view of pharmaceutical efficacy and remain open for improvement in their toxicity and solubility.

Currently, cisplatin which is known as one of effective anticancer agents that are widely used, is particularly effective for treatment of ovarian cancer or testicular cancer and is very contributable to treatment of various kinds of cancers. However, since cisplatin has extremely poor water-soluble and organic-soluble properties in itself, it cannot be easily administered, suggesting limitation in the use thereof. Also, cisplatin disadvantageously has serious toxicity. Attempts to overcome such drawbacks of cisplatin, various anticancer agents are under development, and several thousands of anticancer agents have been synthesized. Some of the synthesized anticancer agents are under clinical trials.

Carboplatin is less toxic than cisplatin, and can be administered to patients in a larger amount, that is, approximately of 2000 mg/dose. However, carboplatin is only effective in treatment of tumor cells resistant to cisplatin, and can only be administered intravenously.

Recently, two platinum complexes have been restrictively authorized as anticancer agents; (trans-L-diaminocyclohexane)oxalatoplatinum (II) (oxaliplatin or L-OHP); and cis-diammine-glycoloato-O,O-platinum (II) (nedaplatin or 254-S). The former platinum complex is currently being used for secondary treatment of metastatic colorectal cancer in Japan and France, while the latter one is authorized to be commercially available in Japan.

However, in clinical testing, oxaliplatin or nedaplatin demonstrated no distinctive efficacy than cisplatin or carboplatin. Only oxaliplatin exhibited potentiality to be used for treatment of tumors resistant to cisplatin in all clinical trials. Research into platinum complexes having enhanced anticancer effects is continuously carried out, with the aim of development of platinum complexes that are less toxic, capable of administrating orally and free of cross resistance to cisplatin and carboplatin.

Existing platinum complex anticancer agents have limitation in improvement of pharmaceutical efficacy by modifying ligand bonded to platinum, and have much room for improvement in view of chemical stability and oral administration.

A novel inclusion compound having 1,1-cyclobutanedicarboxylated diamine platinum (II) (also called "carboplatin") included in alpha-cyclodextrine has been reported. This compound is characterized in that it has a function of increasing water solubility of a platinum complex used as an anticancer agent. However, since a binding constant between alpha-cyclodextrine and carboplatin is low, the binding energy between the two compounds. The inclusion compound is known to have little difference in anticancer effect compared to the case of using only carboplatin.

Technical Goal of the Invention

An object of the present invention is to provide inclusion compounds having metal complexes such as platinum complexes as a guest molecule, and preparation methods thereof.

It is another object of the present invention to provide pharmaceutical composition containing the inclusion compounds.

Structure and Operation of the Invention

The present invention provides an inclusion compound having a cucurbituril derivative of the formula 1 as a host molecule and a metal complex of the formula 2 as a guest molecule:

wherein $R_1$ and $R_2$ are independently selected from the group consisting of H, $C_1$-$C_{30}$ alkyl, $C_1$-$C_{30}$ alkene, $C_1$-$C_{30}$ alkyne, $C_1$-$C_{30}$ alkylthio, $C_1$-$C_{30}$ alkylcarboxy, $C_1$-$C_{30}$ alkylhydroxy, $C_1$-$C_{30}$ alkylsilyl, $C_1$-$C_{30}$ alkyloxy, $C_1$-$C_{30}$ haloalkyl, nitro, $C_1$-$C_{30}$ alkylamine, amine, $C_6$-$C_{30}$ unsubstituted cycloalkyl or $C_5$-$C_{30}$ cycloalkyl having a hetero atom, and $C_6$-$C_{15}$ unsubstituted aryl or $C_6$-$C_{15}$ aryl having a hetero atom, n is an integer from 4 to 20, M is a divalent or quarternary metal ion selected from the group consisting of transition metals, lanthanide metals, actinide metals, alkali metals and alkali earth metals, $X_1$ and $X_2$ meet one selected from the following conditions (i) and (ii):

(i) $X_1$ and $X_2$ are independently selected from the group consisting of halogen atom, $C_1$-$C_{30}$ haloalkyl, hydroxy, $C_1$-$C_{30}$ alkylcarboxy, and $C_1$-$C_{30}$ alkyldicarboxy; or

(ii) $X_1$ and $X_2$ are interconnected to each other and are one among components represented by the structural formulas (a) through (h):

(a)

(b)

(c)

(d)

(e)

(f)

(g)

(h)

$X_3$ and $X_4$ meet one selected from the following conditions (i) and (ii):

(i) when M is a divalent metal ion, $X_3$ and $X_4$ denote non-bonding; or

(ii) when M is a quaternary metal ion, $X_3$ and $X_4$ are independently selected from the group consisting of halogen atom, $C_1$-$C_{30}$ haloalkyl, hydroxy, $C_1$-$C_{30}$ alkylcarboxy, and $C_1$-$C_{30}$ alkyldicarboxy,

$R_3$, $R_4$, $R_5$, $R_6$, $R_7$ and $R_8$ meet one selected from the following conditions (i), (ii) and (iii):

(i) $R_3$, $R_4$, $R_5$, $R_6$, $R_7$ and $R_8$ are independently selected from the group consisting of H, $C_1$-$C_{30}$ alkyl, $C_1$-$C_{30}$ alkene, $C_1$-$C_{30}$ alkyne, $C_1$-$C_{30}$ alkylthio, $C_1$-$C_{30}$ alkylcarboxy, $C_1$-$C_{30}$ alkylhydroxy, $C_1$-$C_{30}$ alkylsilyl, $C_1$-$C_{30}$ alkyloxy, $C_1$-$C_{30}$ haloalkyl, nitro, $C_1$-$C_{30}$ alkylamine, amine, $C_6$-$C_{30}$ unsubstituted cycloalkyl or $C_5$-$C_{30}$ cycloalkyl having a hetero atom, and $C_6$-$C_{15}$ unsubstituted aryl or $C_6$-$C_{15}$ aryl having a hetero atom;

(ii) $R_3$, $R_4$, $R_7$ and $R_8$ are independently selected from the group consisting of H, $C_1$-$C_{30}$ alkyl, $C_1$-$C_{30}$ alkene, $C_1$-$C_{30}$ alkyne, $C_1$-$C_{30}$ alkylthio, $C_1$-$C_{30}$ alkylcarboxy, $C_1$-$C_{30}$ alkylhydroxy, $C_1$-$C_{30}$ alkylsilyl, $C_1$-$C_{30}$ alkyloxy, $C_1$-$C_{30}$ haloalkyl, nitro, $C_1$-$C_{30}$ alkylamine, amine, $C_6$-$C_{30}$ unsubstituted cycloalkyl or $C_5$-$C_{30}$ cycloalkyl having a hetero atom, and $C_6$-$C_{15}$ unsubstituted aryl or $C_6$-$C_{15}$ having a hetero atom, and $R_5$ and $R_6$ are interconnected to each other and one among components represented by the structural formulas (i) through (q):

(i)

(j)

(k)

(l)

-continued (m)

(n)

(p)

(q)

and

(iii) $R_3$, $R_4$ and $R_8$ are independently selected from the group consisting of H, $C_1$-$C_{30}$ alkyl, $C_1$-$C_{30}$ alkene, $C_1$-$C_{30}$ alkyne, $C_1$-$C_{30}$ alkylthio, $C_1$-$C_{30}$ alkylcarboxy, $C_1$-$C_{30}$ alkylhydroxy, $C_1$-$C_{30}$ alkylsilyl, $C_1$-$C_{30}$ alkyloxy, $C_1$-$C_{30}$ haloalkyl, nitro, $C_1$-$C_{30}$ alkylamine, amine, $C_6$-$C_{30}$ unsubstituted cycloalkyl or $C_5$-$C_{30}$ cycloalkyl having a hetero atom, and $C_6$-$C_{15}$ unsubstituted aryl or $C_6$-$C_{15}$ aryl having a hetero atom, and $R_5$ and $R_6$, and $R_6$ and $R_7$ are interconnected to each other and represented by the structural formula (o) wherein asterisk denotes a position bonded with N:

(o)

In the inclusion compound, the binding ratio of the compound of the formula 1 to the metal complex of the formula 2 is preferably in the range of 1:1 to 1:8. In the compound of the formula 1, $R_1$ is hydrogen, methyl, ethyl, propyl, isopropyl, butyl, isobutyl, phenyl or pyridyl, $R_2$ is hydrogen, propyl, phenyl, trichloromethyl, trifluoromethyl, parafluoromethyl or α, α, α-trifluorotoluyl, n is preferably an integer from 5 to 8, and the compound of the formula 2 is represented by formulas 4 through 27:

<Formula 4>

<Formula 5>

<Formula 6>

<Formula 7>

<Formula 8>

<Formula 9>

<Formula 10>

<Formula 11>

<Formula 12>

<Formula 13>

According to another aspect of the present invention, there is provided a method of preparing the inclusion compounds including reacting a cucurbituril derivative of the formula 1 with a metal complex of the formula 2.

In the present invention, the reacting step is performed at room temperature in the presence of a water solvent and includes adding an alcoholic solvent to the resultant product to separate a precipitate. Or, the reacting step is performed at a hydrothermal reactor at a temperature of 80 to 200° C., followed by cooling down to room temperature to separate a crystalline material.

According to still another aspect of the present invention, there is provided a pharmaceutical composition comprising the inclusion composition. Here, The pharmaceutical composition is used for treatment of cancer when the inclusion composition comprises the cucurbituril derivative of the formula 1 as a host molecule and a metal complex represented by the formulas 4 through 27 as a guest molecule.

The inclusion compound of the present invention is represented by the formula 3.

<Formula 3> where, wherein m is and integer from 1 to 8,

<Formula 2> wherein $R_1$ and $R_2$ are independently selected from the group consisting of H, $C_1$-$C_{30}$ alkyl, $C_1$-$C_{30}$ alkene, $C_1$-$C_{30}$ alkyne, $C_1$-$C_{30}$ alkylthio, $C_1$-$C_{30}$ alkylcarboxy, $C_1$-$C_{30}$ alkylhydroxy, $C_1$-$C_{30}$ alkylsilyl, $C_1$-$C_{30}$ alkyloxy, $C_1$-$C_{30}$ haloalkyl, nitro, $C_1$-$C_{30}$ alkylamine, amine, $C_6$-$C_{30}$ unsubstituted cycloalkyl or $C_5$-$C_{30}$ cycloalkyl having a hetero atom, and $C_6$-$C_{15}$ unsubstituted aryl or $C_6$-$C_{15}$ aryl having a hetero atom, n is an integer from 4 to 20, M is a divalent or quarternary metal ion selected from the group consisting of transition metals, lanthanide metals, actinide metals, alkali metals and alkali earth metals, $X_1$ and $X_2$ meet one selected from the following conditions (i) and (ii):

(i) $X_1$ and $X_2$ are independently selected from the group consisting of halogen atom, $C_1$-$C_{30}$ haloalkyl, hydroxy, $C_1$-$C_{30}$ alkylcarboxy, and $C_1$-$C_{30}$ alkyldicarboxy; or

(ii) $X_1$ and $X_2$ are interconnected to each other and are one among components represented by the structural formulas (a) through (h):

(a)

(b)

(c)

(d)

(e)

(f)

(g)

(h)

$X_3$ and $X_4$ meet one selected from the following conditions (i) and (ii):

(i) when M is a divalent metal ion, $X_3$ and $X_4$ denote non-bonding; or (ii) when M is a quaternary metal ion, $X_3$ and $X_4$ are independently selected from the group consisting of halogen atom, $C_1$-$C_{30}$ haloalkyl, hydroxy, $C_1$-$C_{30}$ alkylcarboxy, and $C_1$-$C_{30}$ alkyldicarboxy, $R_3$, $R_4$, $R_5$, $R_6$, $R_7$ and $R_8$ meet one selected from the following conditions (i), (ii) and (iii):

(i) $R_3$, $R_4$, $R_5$, $R_6$, $R_7$ and $R_8$ are independently selected from the group consisting of H, $C_1$-$C_{30}$ alkyl, $C_1$-$C_{30}$ alkene, $C_1$-$C_{30}$ alkyne, $C_1$-$C_{30}$ alkylthio, $C_1$-$C_{30}$ alkylcarboxy, $C_1$-$C_{30}$ alkylhydroxy, $C_1$-$C_{30}$ alkylsilyl, $C_1$-$C_{30}$ alkyloxy, $C_1$-$C_{30}$ haloalkyl, nitro, $C_1$-$C_{30}$ alkylamine, amine, $C_6$-$C_{30}$ unsubstituted cycloalkyl or $C_5$-$C_{30}$ cycloalkyl having a hetero atom, and $C_6$-$C_{15}$ unsubstituted aryl or $C_6$-$C_{15}$ aryl having a hetero atom;

(ii) $R_3$, $R_4$, $R_7$ and $R_8$ are independently selected from the group consisting of H, $C_1$-$C_{30}$ alkyl, $C_1$-$C_{30}$ alkene, $C_1$-$C_{30}$ alkyne, $C_1$-$C_{30}$ alkylthio, $C_1$-$C_{30}$ alkylcarboxy, $C_1$-$C_{30}$ alkylhydroxy, $C_1$-$C_{30}$ alkylsilyl, $C_1$-$C_{30}$ alkyloxy, $C_1$-$C_{30}$ haloalkyl, nitro, $C_1$-$C_{30}$ alkylamine, amine, $C_6$-$C_{30}$ unsubstituted cycloalkyl or $C_5$-$C_{30}$ cycloalkyl having a hetero atom, and $C_6$-$C_{15}$ unsubstituted aryl or $C_6$-$C_{15}$ having a hetero atom, and $R_5$ and $R_6$ are interconnected to each other and one among components represented by the structural formulas (i) through (q):

and (iii) $R_3$, $R_4$ and $R_8$ are independently selected from the group consisting of H, $C_1$-$C_{30}$ alkyl, $C_1$-$C_{30}$ alkene, $C_1$-$C_{30}$ alkyne, $C_1$-$C_{30}$ alkylthio, $C_1$-$C_{30}$ alkylcarboxy, $C_1$-$C_{30}$ alkylhydroxy, $C_1$-$C_{30}$ alkylsilyl, $C_1$-$C_{30}$ alkyloxy, $C_1$-$C_{30}$ haloalkyl, nitro, $C_1$-$C_{30}$ alkylamine, amine, $C_6$-$C_{30}$ unsubstituted cycloalkyl or $C_5$-$C_{30}$ cycloalkyl having a hetero atom, and $C_6$-$C_{15}$ unsubstituted aryl or $C_6$-$C_{15}$ aryl having a hetero atom, and $R_5$ and $R_6$, and $R_6$ and $R_7$ are interconnected to each other and represented by the structural formula (o) wherein asterisk denotes a position bonded with N:

In the formula 3, the binding ratio of the cucurbituril derivative of the formula 1 to the metal complex of the formula 2 is in the range of 1:1 to 1:8, preferably 1:1 to 1:4.

The inclusion compound of the formula 3 is presumably maintained at a stable state such that hydrogen atoms bonded to nitrogen atoms included in the metal complex of the formula 2 form hydrogen bonds with oxygen atoms of the cucurbituril derivative, and hydrophobic substituents bonded to nitrogen atoms in the metal complex of the formula 2 are positioned in hydrophobic cavities.

The preparation of the cucurbituril derivative of the formula 1 was improved by the applicant of the present invention to synthesize and separate cucurbit[6]uril and its homologue cucurbitu[n]uril (n=5, 7 and 8), which was confirmed by X-ray crystal structure determination (U.S. Pat. No. 6,365,734). According to this procedure, unlike the conventional separation method in which only hexametric cucurbituril was separated, pentametric, heptametric and octametric cucurbiturils can be separated, thereby selecting a host molecule according to the size of a guest molecule.

In the formulas 1 and 2, examples of the $C_1$-$C_{30}$ alkyl in $R_1$, $R_2$, $R_3$, $R_4$, $R_5$ and $R_6$, include methyl, ethyl, propyl, isopropyl and tert-butyl, examples of the $C_1$-$C_{30}$ alkenyl include propylene and butene, examples of the $C_1$-$C_{30}$ alkynyl include hexynyl, examples of the $C_1$-$C_{30}$ alkylthio include butylmethyl sulfide and octanethiol, examples of the $C_1$-$C_{30}$ alkylcarboxyl include carboxypropyl and carboxybutyl, examples of the $C_1$-$C_{30}$ hydroxyalkyl include hydroxybutyl and hydroxyethyl, examples of the $C_1$-$C_{30}$ alkylsilyl include allyltriethylsilyl and vinyltriethylsilyl, examples of the $C_1$-$C_{30}$ alkoxy include methoxy and ethoxy, examples of the $C_1$-$C_{30}$ haloalkyl include $CF_3$ and $CH_2Cl$, examples of the $C_1$-$C_{30}$ aminoalkyl include 2-aminobutyl and 1-aminobutyl, examples of the $C_5$-$C_{30}$ unsubstituted cycloalkyl include cyclohexyl and cyclopentyl, examples of the $C_5$-$C_{30}$ cycloalkyl having a hetero atom include piperidyl and tetrahydrofuranyl, examples of $C_6$-$C_{30}$ unsubstituted aryl include phenyl, benzyl and naphthyl, and examples of $C_6$-$C_{30}$ aryl having a hetero atom include pentafluorophenyl or pyridyl. In $X_1$, $X_2$, $X_3$ and $X_4$, examples of the halogen atom include Br, Cl, I and F, examples of the $C_1$-$C_{30}$ haloalkyl include bromomethyl and chloromethyl, examples of the $C_1$-$C_{30}$ alkylcarboxyl include $CH_3C(=O)O-$, and example of $C_1$-$C_{30}$ alkyldicarboxy include oxalato and malonato.

In M, examples of the transition metal include Pt, Pd and Au, examples of the lanthanide metal include Ln, Gd and Ce, examples of the actinide metals include Ac, examples of the alkali metal include Li, Na and K, and examples of the alkali earth metal include Mg and Ca.

The cucurbituril derivatives of the formula 1 is good in solubility in general solvents. In the cucurbituril derivatives of the formula 1, in particular, $R_1$ is preferably methyl, ethyl, propyl, isopropyl, butyl, isobutyl, phenyl or pyridyl, $R_2$ is preferably hydrogen, propyl, phenyl, trichloromethyl, trifluoromethyl, parafluoromethyl or α, α, α-trifluorotoluyl, and n is preferably an integer from 5 to 8. In cucurbituril derivatives of the formula 1, it is more preferable that $R_1$ and $R_2$ are both hydrogen and n is in the range from 5 to 8. These compounds have a water-solubility of $1\times10^{-1}$ to $3\times10^{-1}$ M, and have a good solubility in an organic solvent, in particular, in one selected from the group consisting of methanol, ethanol, dimethylsulfoxide, dimethylformamide and acetonitrile, that is, $1\times10^{-4}$ to $1\times10^{-2}$ M.

In the case where M is a divalent platinum ion, and $X_3$ and $X_4$ denote non-bonding, examples of the complex of the formula 2 include cisplatin of the formula 4 wherein $X_1$ and $X_2$ are both Cl, and $R_3$ through $R_8$ are all H, carboplatin of the formula 5 wherein $X_1$ and $X_2$ are both Cl, and $X_3$ and $X_4$ are represented by the structural formula a, and $R_3$ through $R_8$ are all H, oxaliplatin of the formula 6 wherein $R_3$, $R_4$, $R_6$ and $R_7$ are all H, $R_5$ and $R_6$ are represented by the structural formula j, and $X_1$ and $X_2$ are represented by the structural formula b, JM118 of the formula 7 wherein $X_1$ and $X_2$ are both Cl, $R_3$, $R_4$, $R_5$, $R_7$ and $R_8$ are all H, and $R_6$ is represented by the structural formula j, Pt(cis-1,4-dach)Cl$_2$, of the formula 8 (Here, dach represents 1,2-diaminocyclohexyl or 1,2-diaminocyclohexane) wherein $X_1$ and $X_2$ are both Cl, $R_3$, $R_4$, $R_7$ and $R_8$ are all H, and $R_5$ and $R_6$ are interconnected to each other and represented by the structural formula i, xeniplatin of the formula 9 wherein $X_1$ and $X_2$ are both Cl, $R_3$, $R_4$, $R_7$ and $R_8$ are all H, and $R_5$ and $R_6$ are represented by the structural formula k, enloplatin of the formula 10 wherein $X_1$ and $X_2$ are interconnected to each other and represented by the structural formula a, $R_3$, $R_4$, $R_7$ and $R_8$ are all H, and $R_5$ and $R_6$ are interconnected to each other and represented by the structural formula l, Cl-973 of the formula 11 wherein $X_1$ and $X_2$ are interconnected to each other and represented by the structural formula m, $R_3$, $R_4$, $R_7$ and $R_8$ are all H, and $R_5$ and $R_6$ are interconnected to each other and represented by the structural formula a, cycloplatam of the formula 12 wherein $X_1$ and $X_2$ are interconnected to each other and represented by the structural formula f and $R_3$, $R_4$, $R_6$, $R_7$ and $R_8$ are all H, and $R_5$ is cyclopentyl, SKI 2053R of the formula 13 wherein $X_1$ and $X_2$ are interconnected to each other and represented by the structural formula c, $R_3$, $R_4$, $R_7$ and $R_8$ are all H, and $R_5$ and $R_6$ are represented by the structural formula n, miboplatin of the formula 14 wherein $X_1$ and $X_2$ are interconnected to each other and represented by the structural formula a, $R_3$, $R_4$ and $R_8$ are all H, and $R_5$, $R_6$ and $R_7$ are represented by the structural formula o, iobaplatin of the formula 15 wherein $X_1$ and $X_2$ are interconnected to each other and represented by the structural formula g, $R_3$, $R_4$, $R_7$ and $R_8$ are all H, and $R_5$ and $R_6$ are represented by the structural formula p, L-NDDP of the formula 16 wherein $X_1$ and $X_2$ are both $C_9H_{19}$. $R_3$, $R_4$, $R_7$ and $R_8$ are all H, and $R_5$ and $R_6$ are interconnected to each other and represented by the structural formula j, TRK-710 of the formula 17 wherein $X_1$ and $X_2$ are interconnected to each other and represented by the structural formula h, $R_3$, $R_4$, $R_7$ and $R_8$ are all H, and $R_5$ and $R_6$ are interconnected to each other and represented by the structural formula j, and Na[Pt(R,R-dach)(MPBA)] of the formula 18 wherein $X_1$ and $X_2$ are interconnected to each other and represented by the structural formula d, $R_3$, $R_4$, $R_7$ and $R_8$ are all H, and $R_5$ and $R_6$ are interconnected to each other and represented by the structural formula j.

In the case where $X_3$ and $X_4$ represent various kinds of substituents, examples of the of the complex of the formula 2 include cisdiaminedichloroplatinium (IV) of the formula 19 wherein $X_1$, $X_2$, $X_3$ and $X_4$ are all Cl, $R_3$, $R_4$, $R_5$, $R_6$, $R_7$ and $R_8$ are all H, JM216 of the formula 20 wherein $X_1$ and $X_2$ are both Cl, $X_3$ and $X_4$ are both OC(=O)CH$_3$, $R_3$, $R_4$, $R_5$, $R_7$ and $R_8$ are all H, and $R_6$ are cyclohexyl, iprolatin of the formula 21 wherein $X_1$ and $X_2$ are both Cl, $X_3$ and $X_4$ are both OH, $R_3$, $R_4$, $R_7$ and $R_8$ are all H, $R_5$ and $R_6$ are both isopropyl, omaplatin of the formula 22 wherein $X_1$, $X_2$, $X_3$ and $X_4$ are all Cl, $R_3$, $R_4$, $R_5$, $R_7$ and $R_8$ are all H, and $R_5$ and $R_6$ are interconnected to each other and represented by the structural formula j, JM221 of the formula 23 wherein $X_1$ and $X_2$ are both Cl, $X_3$ and $X_4$ are both —OC(=O)CH$_2$CH$_2$CH$_3$, $R_3$, $R_4$, $R_5$, $R_7$ and $R_8$ are all H, and $R_6$ is cyclohexyl, JM149 of the formula 24 wherein $X_1$ and $X_2$ are both Cl, $X_3$ and $X_4$ are both OH, $R_3$, $R_4$, $R_5$, $R_7$ and $R_8$ are all H, and $R_6$ is cyclohexyl, JM518 of the formula 25 wherein $X_1$ is OH, $X_2$ is Cl, $X_3$ and $X_4$ are both —OC(=O)CH$_3$, $R_3$, $R_4$, $R_5$, $R_7$ and $R_8$ are all H, and $R_6$ is cyclohexyl, JM383 of the formula 26 wherein $X_1$ and $X_2$ are both OH, $X_3$ and $X_4$ are both —OC(=O)CH$_3$, $R_3$, $R_4$, $R_5$, $R_7$ and $R_8$ are all H, and $R_6$ is cyclohexyl, and JM335 of the formula 27 wherein $X_1$ is NH$_3$, $X_2$ is Cl, $X_3$ and $X_4$ are both OH, $R_3$, $R_4$, $R_5$, $R_7$ and $R_8$ are both H, and $R_6$ is cyclohexyl.

Preparation methods of the inclusion compounds of the formula 3 according to the present invention will now be described.

The inclusion compounds of the formula 3 can be obtained by mixing the cucurbituril derivatives of the formula 1 with the metal complexes of the formula 2, followed by stirring and reacting.

The reaction is carried out by stirring the reactants at room temperature for 1 to 6 hours in the presence of water as a solvent, or reacting in a hydrothermal reactor at 80 to 200° C., in particular, 100 to 120° C., for 1 to 3 days and then being allowed to stand at 50 to 70° C. for 1 to 2 days.

During the hydrothermal reaction, the reaction is preferably carried out in the above-noted temperature range in view of reactivity. A work-up procedure resulting from the reaction will now be briefly described. After reacting at room temperature, an alcoholic solvent such as methanol or ethanol is added to the reaction product to separate the resultant in the form of precipitate. During the reaction carried out at the hydrothermal reactor, the reaction product is cooled to room temperature to then precipitate in a crystalline form.

In preparing the inclusion compounds of the formula 3, the binding ratio of the cucurbituril derivative of the formula 1 to the metal complex of the formula 2 can be adjusted according to equivalents in consideration of sizes of cavities of cucurbituril. Preferably, 1 to 10 quivalents of the metal complex of the formula 2 is used based on one equivalent of the cucurbituril derivative of the formula 1.

The pharmaceutical composition according to the present invention includes the inclusion compound of the formula 3. The inclusion compound is contained in the pharmaceutical composition in a pharmaceutically effective amount. In the case of using a platinum complex, e.g., cisplatin, as the metal complex of the formula 2, the inclusion compound can be advantageously used as an anticancer agent. The anticancer agent can prevents the platinum complex as an effective component from being biologically degraded in vivo and can exhibit continuous drug effect for a long time just by a single dosage by controlling the release time of the platinum complex once it reaches target tumor cells.

The pharmaceutical composition of this invention can be administered to humans or animals orally or non-orally. For example, the inclusion compound dissolved or suspended in an injection solvent such as injection water, a saline solution, 5% glucose aqueous solution, aqueous ethanol, aqueous glycerine or aqueous propylene glycol, in the form of, for example, intravenous injection, intramuscular injection, subcutaneous injection or instillation.

In the pharmaceutical composition of the invention, formulations include tablets, capsules, soft capsules, liquid preparations, powdery preparations and the like. The formulations in the state of a solution or a suspension can be preserved in sealed ampoules or vials, in the form of, for example, granules, powders, microgranules or freeze dried preparations for being dissolved directly before use. A stabilizer may be further added to the formulations.

When the pharmaceutical composition of the invention, including the inclusion compound and metal complexes such as the compounds represented by the formulas 4-27, is administered for treatment of cancer, its daily dose for adult person is substantially the same as that of an anticancer agent, for example, in an amount of approximately 2000 mg/dose, typically once a week or every 3 or 4 weeks, which can be administered orally or non-orally.

The pharmaceutical composition of the invention can be advantageously used for treatment of various types of cancers such as ovarian cancer, breast cancer or colonic cancer.

Various kinds of pharmaceutically acceptable additives can be further added to the pharmaceutical composition according to the invention, and the concentration thereof may vary depending on the addition purposes.

The present invention is illustrated in more detail by the following examples without, however, being limited thereby.

EXAMPLES

Synthesis Example 1

Synthesis of Inclusion Compound of Oxaliplatin and Cucurbitu[7]ril 3 mg of oxaliplatin and 9 mg of cucurbitu[7]ril were added to 20 mL water and hydrothermally reacted at 100° C. for 24 hours at a hydrothermal reactor with a reaction vessel made of Teflon. The reaction mixture was slowly cooled down to room temperature to give a colorless, plate-shaped crystalline material. The crystalline material was then filtered and dried in the presence of air, thereby obtaining an inclusion compound at a yield of 61%.

Synthesis Example 2

Synthesis of Inclusion Compound of Oxaliplatin and Cucurbitum[7]ril 3 mg of oxaliplatin and 9 mg of cucurbitu[7]ril were added to 20 mL water and reacted, and then ethanol was added to the mixture to form a precipitate. Thereafter, the precipitate was filtered and dried in the presence of air, thereby obtaining an inclusion compound at a yield of 72%.

The inclusion compounds synthesized in Synthesis Examples 1 and 2 were subjected to analysis by NMR (500 MHz), CHNS determination and Mass spectrometry, respectively, and the results thereof are:

$^1$H NMR (500 MHz, $D_2O$) 2.26(2H, m), 1.96-1.98(2H, m), 1.60-1.62(2H, m), 1.21-1.23(2H, m), 1.07-1.09(2H, m)

Elemental analysis $\{(C_8H_{14}N_2O_4Pt)(C_{42}H_{42}N_{28}O_{14})\} \cdot 8H_2O$ Cald. C 34.87; H, 4.33; N, 24.40

Found C, 34.47; H, 4.43; N, 24.65

ESI-MS m/z $[M+2Li]^{2+}$ 786.7 (Cald: 787.3), $[M+2Li+DMF]^{2+}$ 823.3 (Cald: 823.2), $[M+Li]^+$ 1566.5 (Cald: 1566.5), $[M+Li+LiI]^+$ 1700.5 (Cald: 1700.3), $[M+Li+2LiI]^{2+}$ 1834.4 (cald: 1834.3), $[M+Li+3LiI]^{3+}$ 1968.4 (Cald: 1968.1)

Figure 1:
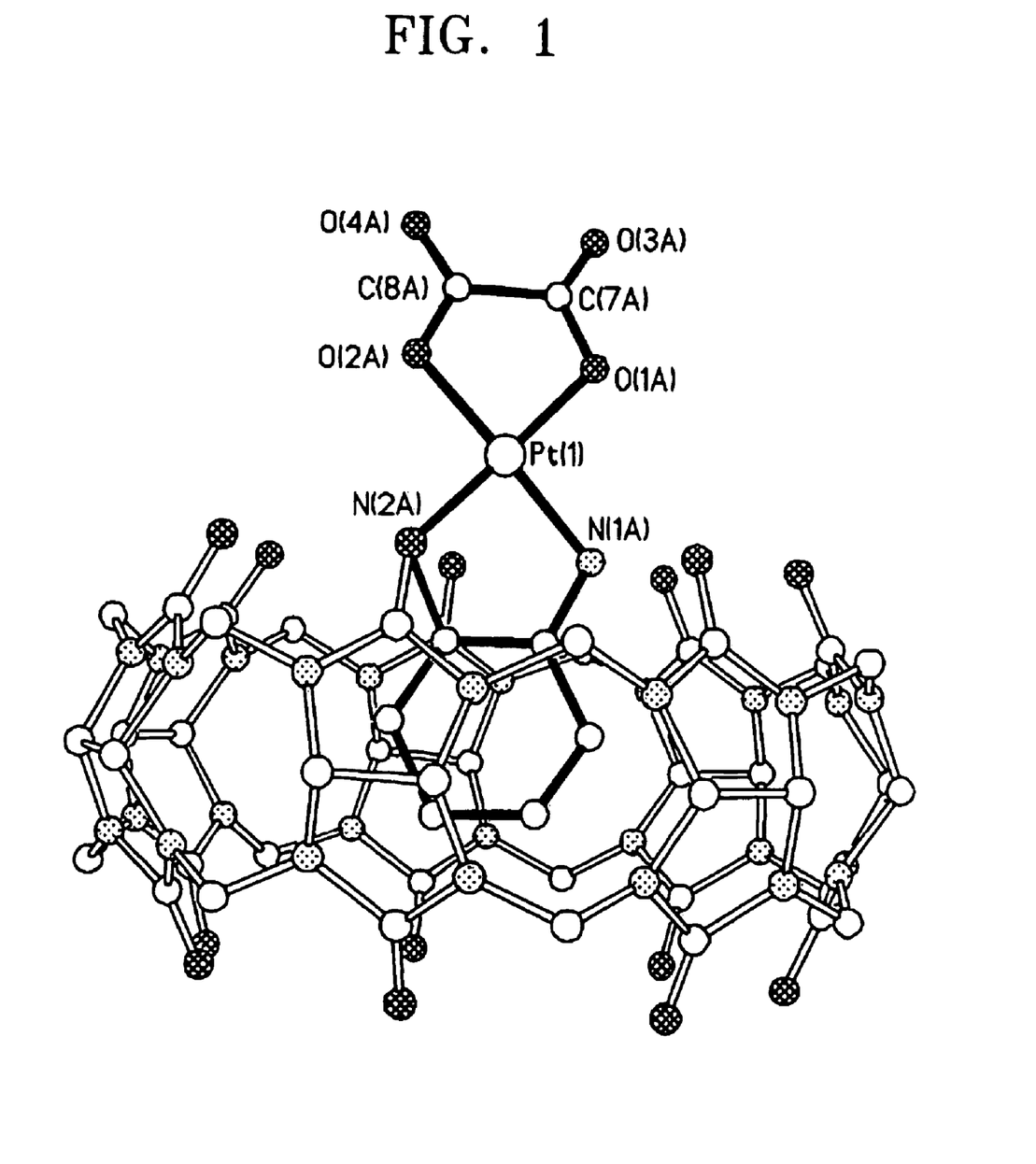
FIG. 1 is a diagram of the X-ray crystal structure of an inclusion compound according to Synthesis Example 1 of the present invention.

Also, the X-ray crystal structure of the inclusion compound was investigated, and the result thereof is shown in FIG. 1.

FIG. 1 shows X-ray crystal structure of the inclusion compound, and data thereof are listed below:

$C_{50}H_{81.33}N_{30}O_{31.67}Pt$, m/w=1804.54, Orthorhombic, Space group $P2_12_12_1$, a=23.6543(5), b=30.23670(10), c=31.2827(6), Volume=22374.3(6), $R_1$=0.1093

Referring to FIG. 1, the inclusion compound contains cucurbitu[7]ril as a host molecule and oxaliplatin as a guest molecule, in a binding ratio of 1:1. According to observation of the host-guest molecular structure, an amine atom of the guest molecule, that is, oxaliplatin, was maintained at the same geometric level as an oxygen atom of the host molecule, that is, cucurbituril. Also, a hydrogen bond was established between a hydrogen atom connected to the ammine of oxaliplatin and an oxygen atom of cucurbituril, and the cyclohexyl of the oxaliplatin is encapsulated in a hydrophobic capvity. In such a manner, a stable inclusion compound was formed.

Figure 2:
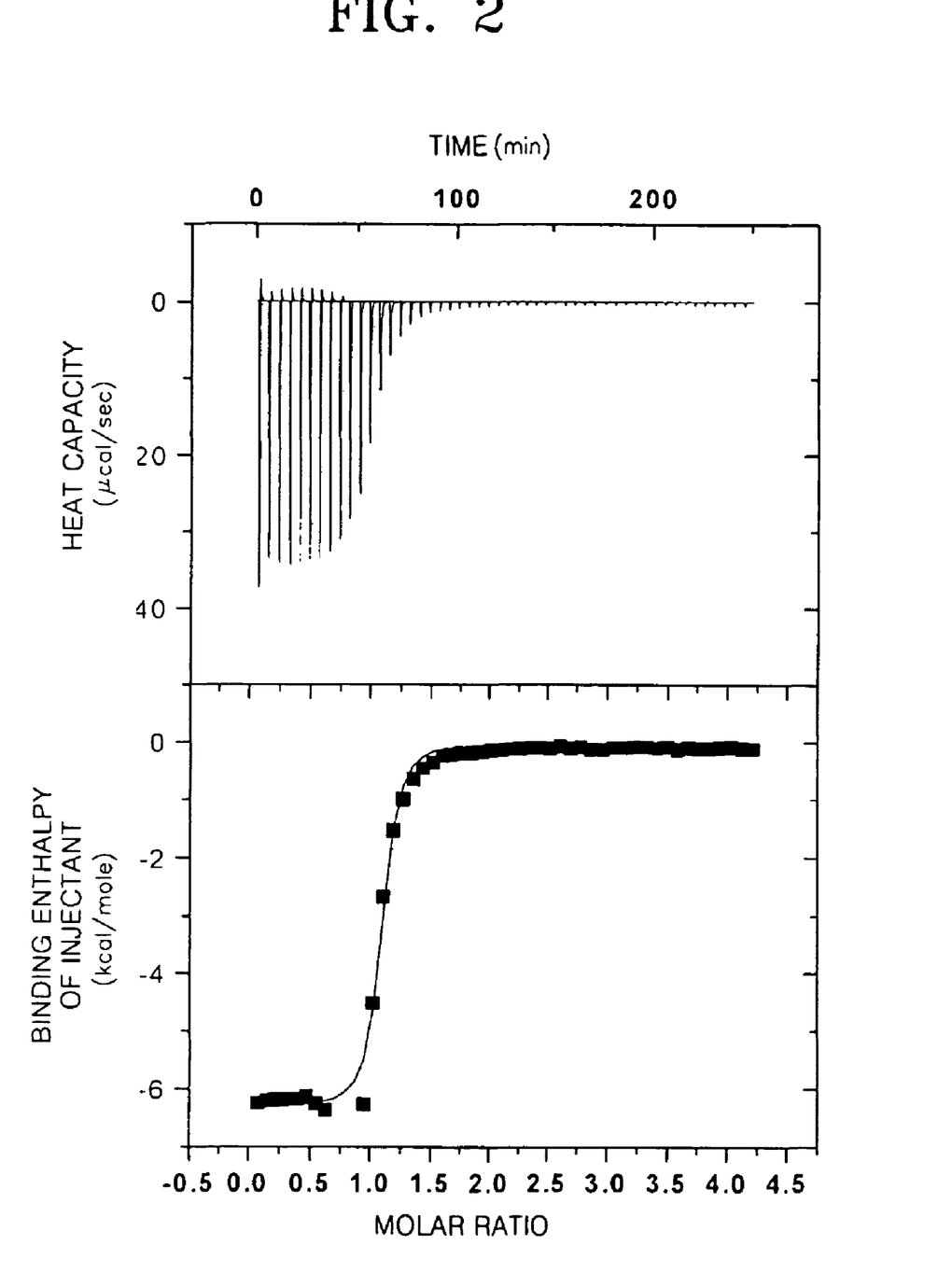
FIG. 2 is a titration graph of the inclusion compound according to Synthesis Example 1 of the present invention, measured by an isothermal microcalorimeter.

The inclusion compounds synthesized in Synthesis Examples 1 and 2 were subjected to analysis by an isothermal microcalorimeter to measure binding constants of oxaliplatin and cucurbitu[7]ril, and the results thereof are shown in FIG. 2. The experiment was carried out under a constant temperature condition of 25° C., with concentrations of 20 mM oxaliplatin and 1 mM cucurbitu[7]ril.

As a result, oxaliplatin and cucurbituril derivative had a binding constant of $2.39 \times 10^5 (\pm 0.4)$ $M^{-1}$, a binding enthalpy of −6.33 kcal/mole (±0.07), and entropy of 3.31 esu. Such a relatively high binding constant of oxaliplatin and cucurbituril, compared to $60 M^{-1}$ of Stoddart group, suggests a very strong bond between host-guest molecules. Also, the positive entropy value confirms that the reaction is entropically advantageous as water molecule trapped by the host molecule escapes during a binding process.

Synthesis Example 3

Synthesis of Inclusion Compound of Oxaliplatin and Cucurbitu[8]ril 13 mg of cucurbitu[8]ril and 3 mg of oxaliplatin were added to 10 mL water and hydrothermally reacted at 100° C. for 24 hours, followed by slowly cooling to give a crystalline material. The crystalline material was then filtered, followed by drying in the presence of air, thereby obtaining 6 mg of an inclusion compound at a yield of 75%.

Synthesis Example 4

Synthesis of Inclusion Compound of Oxaliplatin and Cucurbitu[8]ril 13 mg of cucurbitu[8]ril and 3 mg of oxaliplatin were added to 10 mL water and stirred at room temperature, followed by adding methanol thereto to induce precipitation. The resultant precipitate was filtered and dried in the presence of air, thereby obtaining 6 mg of an inclusion compound at a yield of 78%.

In the inclusion compounds synthesized in Synthesis Examples 3 and 4, oxaliplatin and cucurbitu[8]ril were contained in a binding ratio of 2:1.

Synthesis Example 5

Synthesis of Inclusion Compound of cis-dichloroethylenediamine Platinum (II) and Cucurbitur[7]ril

3 mg of cis-dichloroethylenediamineplatinum (II) and 9 mg of cucurbitu[7]ril were added to 10 mL water and hydrothermally reacted at 100° C., followed by slowly cooling down, filtering and drying in the presence of air, thereby obtaining 5 mg of an inclusion compound at a yield of 65%.

Synthesis Example 6

Synthesis of Inclusion Compound of cis-dichloroethylenediamine Platinum (II) and Cucurbitu[7]ril

3 mg of cis-dichloroethylenediamineplatinum (II) and 9 mg of cucurbitu[7]ril were added to 10 mL water and stirred at room temperature, followed by adding methanol thereto to induce precipitation. The resultant precipitate was filtered and dried in the presence of air, thereby obtaining 5 mg of a solid inclusion compound at a yield of 65%.

Synthesis Example 7

Synthesis of Inclusion Compound of cis-dichloroethylenediamine Platinum (II) and Cucurbitu[8]ril

3 mg of cis-dichloroethylenediamineplatinum (II) and 7 mg of cucurbitu[8]ril were added to 10 mL water and hydrothermally reacted at 100° C. for 24 hours. As a result, the resultant crystalline material was filtered and dried in the presence of air, thereby obtaining 5 mg of an inclusion compound at a yield of 68%.

Synthesis Example 8

Synthesis of Inclusion Compound of cis-dichloroethyldiamine Platinum (II) and cucurbitu[8]ril

3 mg of cis-dichloroethylenediamine platinum (II) and 7 mg of cucurbitu[8]ril were added to 10 mL water and stirred at room temperature. Then, methanol was added to the reaction product to form a precipitate.

Thereafter, the precipitate was filtered and dried in the presence of air, thereby obtaining 5 mg of a solid inclusion compound at a yield of 65%.

Anticancer activities of the inclusion compounds synthesized in Synthesis Examples 1 and 2 were measured as follows.

First, the oxaliplatin-cucurbitu[7]ril inclusion compounds synthesized in Synthesis Examples 1 and 2, were freeze-dried to prepare samples. Tumor cells used were A 549 (human non-small cell lung), SKOV-3 (human ovarian), SKMEL-2 (human melanoma), XF498 (human CNS), and HCT-15 (human colon), and analyzed by SRB (sulforhodamine B) assay. The analysis results are shown in Table 1.

TABLE 1

| | Antiproliferative activity ($ED_{50}/\mu M$) | | |
|---|---|---|---|
| Cell line[a] | Cisplatin | Oxaliplatin[b] | Inclusion compounds between oxaliplatin and CB[7][b] |
| A549 | 1.17 | 0.42 | 2.43 |
| SKOV-3 | 2.87 | 0.67 | 4.88 |
| SKMEL-2 | 3.08 | 0.97 | 18.71 |
| XF-498 | 0.46 | 0.49 | 4.94 |
| HCT-15 | 1.32 | 0.90 | 13.26 |

[a] A549 human non-small cell lungs; SKOV-3 human ovarian; SKMEL-2 human melanoma; XF-498 human CNS; HCT-15 human colon,
[b] Good water-solubility As shown in Table 1, the oxaliplatin-cucurbitu[7]ril inclusion compounds synthesized in Synthesis Examples 1 and 2 exhibited good antiproliferative activities, which is presumably due to strong coordination of oxaliplatin to cucurbitu[7]ril. Also, since the inclusion compounds have capability of slowly releasing oxaliplatin, it was confirmed that continuous drug effect could be exhibited for a long time just by a single dosage of the pharmaceutical composition.

EFFECT OF THE INVENTION

The inclusion compound according to the present invention include a cucurbituril derivative of the formula 1 as a host molecule and a metal complex of the formula 2 as a guest molecule. A pharmaceutical composition having an anticancer effect can be obtained by using the inclusion compound according to the present invention. The pharmaceutical composition can prevent effective components from being biologically degraded in vivo and can exhibit continuous drug effect for a long time just by a single dosage by controlling the release time of the platinum complex once it reaches target tumor cells.

What is claimed is:
1. An inclusion compound having a cucurbituril derivative of the formula 1 as a host molecule and a metal complex of the formula 2 as a guest molecule:

wherein $R_1$ and $R_2$ are independently selected from the group consisting of H, $C_1$-$C_{30}$ alkyl, $C_1$-$C_{30}$ alkene, $C_1$-$C_{30}$ alkyne,

$C_1$-$C_{30}$ alkylthio, $C_1$-$C_{30}$ alkylcarboxy, $C_1$-$C_{30}$ alkylhydroxy, $C_1$-$C_{30}$ alkylsilyl, $C_1$-$C_{30}$ alkyloxy, $C_1$-$C_{30}$ haloalkyl, nitro, $C_1$-$C_{30}$ alkylamine, amine, $C_5$-$C_{30}$ unsubstituted cycloalkyl or $C_5$-$C_{30}$ cycloalkyl having a hetero atom, and $C_6$-$C_{15}$ unsubstituted aryl or $C_6$-$C_{15}$ aryl having a hetero atom, n is an integer from 4 to 20, M is a divalent or quartemary metal ion selected from the group consisting of transition metals, lanthanide metals, actinide metals, alkali metals and alkali earth metals, $X_1$ and $X_2$ meet one selected from the following conditions (i) and (ii): (i) $X_1$ and $X_2$ are independently selected from the group consisting of halogen atom, $C_1$-$C_{30}$ haloalkyl, hydroxy, $C_1$-$C_{30}$ alkylcarboxy, and $C_1$-$C_{30}$ alkyldicarboxy; or (ii) $X_1$ and $X_2$ are interconnected to each other and are one among components represented by the structural formulas (a) through (h):

(a)

(b)

(c)

(d)

(e)

(f)

-continued (g)

(h)

$X_3$ and $X_4$ meet one selected from the following conditions (i) and (ii): (i) when M is a divalent metal ion, $X_3$ and $X_4$ denote non-bonding; or (ii) when M is a quaternary metal ion, $X_3$ and $X_4$ are independently selected from the group consisting of halogen atom, $C_1$-$C_{30}$ haloalkyl, hydroxy, $C_1$-$C_{30}$ alkylcarboxy, and $C_1$-$C_{30}$ alkyldicarboxy, $R_3$, $R_4$, $R_5$, $R_6$, $R_7$ and $R_8$ meet one selected from the following conditions (i), (ii) and (iii): (i) $R_3$, $R_4$, $R_5$, $R_6$, $R_7$ and $R_8$ are independently selected from the group consisting of H, $C_1$-$C_{30}$ alkyl, $C_1$-$C_{30}$ alkene, $C_1$-$C_{30}$ alkyne, $C_1$-$C_{30}$ alkylthio, $C_1$-$C_{30}$ alkylcarboxy, $C_1$-$C_{30}$ alkylhydroxy, $C_1$-$C_{30}$ alkylsilyl, $C_1$-$C_{30}$ alkyloxy, $C_1$-$C_{30}$ haloalkyl, nitro, $C_1$-$C_{30}$ alkylamine, amine, $C_6$-$C_{30}$ unsubstituted cycloalkyl or $C_5$-$C_{30}$ cycloalkyl having a hetero atom, and $C_6$-$C_{15}$ unsubstituted aryl or $C_6$-$C_{15}$ aryl having a hetero atom; (ii) $R_3$, $R_4$, $R_7$ and $R_8$ are independently selected from the group consisting of H, $C_1$-$C_{30}$ alkyl, $C_1$-$C_{30}$ alkene, $C_1$-$C_{30}$ alkyne, $C_1$-$C_{30}$ alkylthio, $C_1$-$C_{30}$ alkylcarboxy, $C_1$-$C_{30}$ alkylhydroxy, $C_1$-$C_{30}$ alkylsilyl, $C_1$-$C_{30}$ alkyloxy, $C_1$-$C_{30}$ haloalkyl, nitro, $C_1$-$C_{30}$ alkylamine, amine, $C_6$-$C_{30}$ unsubstituted cycloalkyl or $C_5$-$C_{30}$ cycloalkyl having a hetero atom, and $C_6$-$C_{15}$ unsubstituted aryl or $C_6$-$C_{15}$ aryl having a hetero atom, and $R_5$ and $R_6$ are interconnected to each other and one among components represented by the structural formulas (i) through (q):

(i)

(j)

(k)

(l)

-continued and (iii) $R_3$, $R_4$ and $R_8$ are independently selected from the group consisting of H, $C_1$-$C_{30}$ alkyl, $C_1$-$C_{30}$ alkene, $C_1$-$C_{30}$ alkyne, $C_1$-$C_{30}$ alkylthio, $C_1$-$C_{30}$ alkylcarboxy, $C_1$-$C_{30}$ alkylhydroxy, $C_1$-$C_{30}$ alkylsilyl, $C_1$-$C_{30}$ alkyloxy, $C_1$-$C_{30}$ haloalkyl, nitro, $C_1$-$C_{30}$ alkylamine, amine, $C_6$-$C_{30}$ unsubstituted cycloalkyl or $C_5$-$C_{30}$ cycloalkyl having a hetero atom, and $C_6$-$C_{15}$ unsubstituted aryl or $C_6$-$C_{15}$ aryl having a hetero atom, and $R_5$ and $R_6$, and $R_6$ and $R_7$ are interconnected to each other and represented by the structural formula (o) wherein asterisk denotes a position bonded with N:

(o)

2. The inclusion compound according to claim 1, wherein the binding ratio of the compound of the formula 1 to the metal complex of the formula 2 is in the range of 1:1 to 1:8.

3. The inclusion compound according to claim 1, wherein the binding ratio of the compound of the formula 1 to the metal complex of the formula 2 is in the range of 1:1 to 1:4.

4. The inclusion compound according to claim 1, wherein in the compound of the formula 1, $R_1$ is hydrogen, methyl, ethyl, propyl, isopropyl, butyl, isobutyl, phenyl or pyridyl, $R_2$ is hydrogen, propyl, phenyl, trichloromethyl, trifluoromethyl, parafluoromethyl and α, α, α-trifluorotoluyl, and n is an integer from 5 to 8.

5. The inclusion compound according to claim 1, wherein in the compound of the formula 2, M is one selected from the group consisting of gold (Au), platinum (Pt) and palladium (Pd).

6. The inclusion compound according to claim 1, wherein the compound of the formula 2 is represented by formulas 4 through 27:

<Formula 4>

<Formula 5>

<Formula 6>

<Formula 7>

<Formula 8>

<Formula 9>

<Formula 10>

<Formula 11>

<Formula 12>

<Formula 13>

-continued

7. A method of preparing the inclusion compound according to claim 1, comprising the step of reacting the cucurbituril derivative of the formula 1 with the metal complex of the formula 2.

8. The method according to claim 7, wherein the reacting step is performed at room temperature in the presence of a water solvent and includes adding an alcoholic solvent to the resultant product to separate a precipitate.

9. The method according to claim 7, wherein the reacting step is performed at a hydrothermal reactor at a temperature of 80 to 200° C., followed by cooling down to room temperature to separate a crystalline material.

10. A pharmaceutical composition comprising the inclusion composition according to claim 1, the inclusion composition comprising the cucurbituril derivative of the formula 1 as a host molecule and a metal complex of the formula 2 as a guest molecule.

* * * * *